United States Patent [19]

Greif

[11] Patent Number: 4,813,344
[45] Date of Patent: Mar. 21, 1989

[54] DEODORIZER CONTAINER

[76] Inventor: Averell Greif, 500 Newfield Ave., Apt. 2H, Stamford, Conn. 06905

[21] Appl. No.: 39,977

[22] Filed: Apr. 20, 1987

[51] Int. Cl.$^4$ ............................................. B60H 1/32
[52] U.S. Cl. ...................................... 98/2.11; 422/124
[58] Field of Search ................... 98/2.11, 40.24, 105, 98/109; 422/123, 124; 239/57, 58, 59; 34/60

[56] References Cited

U.S. PATENT DOCUMENTS 2,738,225  3/1956  Meek ..................................... 239/59
4,523,870  6/1985  Spector ................................ 98/2.11

Primary Examiner—Henry A. Bennet
Attorney, Agent, or Firm—Philip Furgang

[57] ABSTRACT

The bottom and cooperating cover of a deodorizer container are of a size and configuration particularly adapting same for deployment between the louvres of an air moving device such as the ducts of an auto air conditioner. The container bottom stores a deodorizing agent. The container cover is deployed on the container bottom and includes teats formed in sides of the cover proximate an end to fit within the grooves formed in sides of the bottom. The cover also has a tab extending from one of its sides to facilitate sliding the cover between open and closed positions. The container bottom is a six-sided box with openings in its top surface and grooved sides for movement of air and deodorant therethrough. Additionally, the grooved sides have detents which engage the teats and prevent the cover from coming off. A bottom surface of the bottom container may be releasably attached to a blade of a louvre of an air conditioning device or system by Velcro tape or the like.

15 Claims, 2 Drawing Sheets

FIG. 1
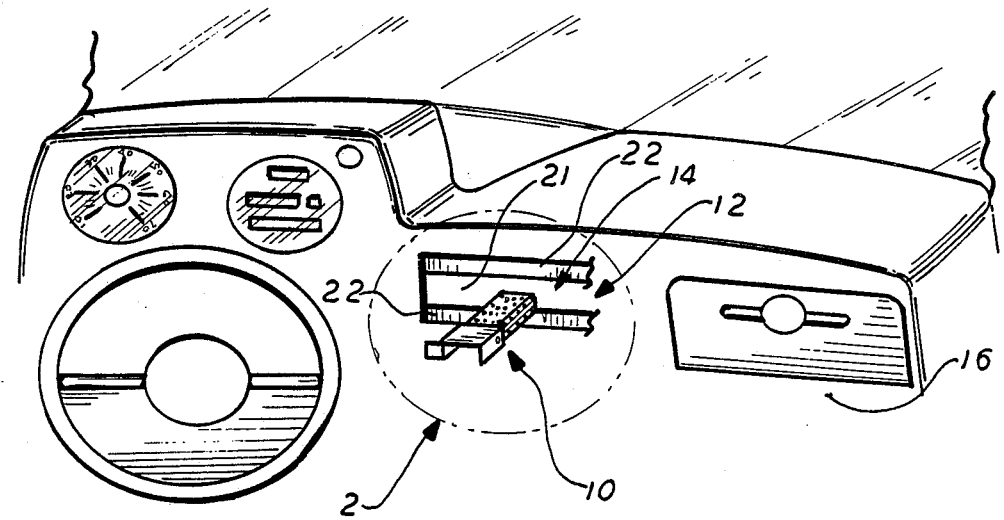
FIG. 2
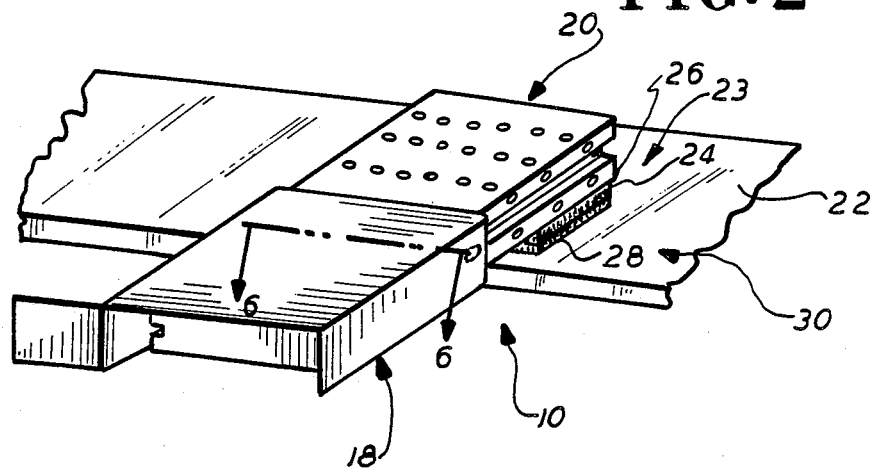
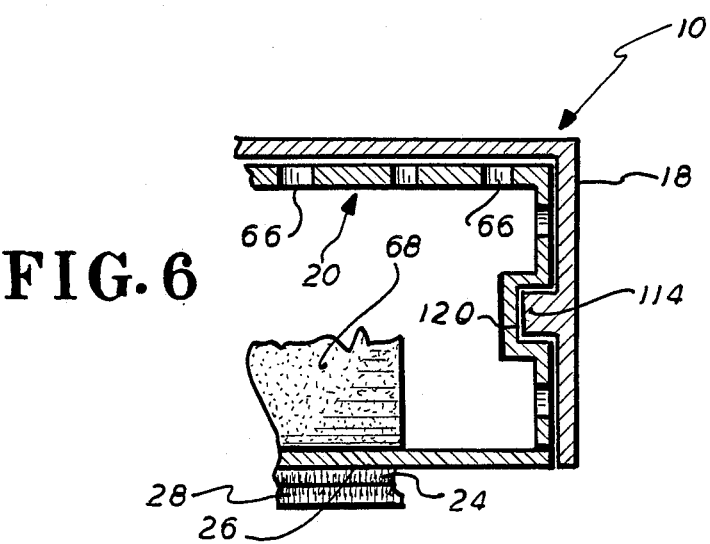
FIG. 6

DEODORIZER CONTAINER

BACKGROUND OF THE INVENTION-FIELD OF APPLICATION

This invention relates to deodorizers and more particularly to deodorizers deployed in a container.

BACKGROUND OF THE INVENTION-DESCRIPTION OF PRIOR ART

Deodorizers of various types have generally been available for quite sometime. They have had extensive application in commercial, industrial and home use. The deodorizers themselves have taken the form of solids, liquids, gels and similar substances. They are usually housed in a release mechanism, package, container, etc. which encloses the deodorizer so that it is alternatively either not exposed to the atmosphere, or so that it permits exposure thereof to the atmosphere and escape of the deodorizing substance into the surrounding area.

The liquid deodorizers available since the early to mid 1950's were usually dispensed from containers in the form of glass bottles with a wire framed wick deployed therein. This absorbent wick usually was immersed in the liquid deodorant and the deodorizer was released by removing a releasable twist cap and extending the wick from the neck of the bottle. The rate of dispersion for this type device seems to have been slow and it required attention regarding reclosure of the container or there would be resultant waste of product. The possiblity of spills and breakage also rendered this type of deodorizer unsuitable for many applications.

Gel formed deodorizer products, which sublime in air continuously, have also been made available as have spray dispensers utilized for the removal, neutralizing or masking of ordors. The use of fluorocarbons as a delivery means resulted in the discontinuation of many deodorant sprays.

Air fresheners have also been dispensed into the air by a forced air flow rather than the normal movement of the atmosphere, some examples of this are shown in U.S. Pat. No. 4,301,095 granted to Leo Mettler et al, on Nov. 11, 1981 for *Air Freshener Dispenser* and U.S. Pat. No. 4,383,377 granted to Thomas Crafton on May 17, 1983 for *Hot Air Dryer Room Deodorizer*. This approach seems to be most applicable to restroom applications and would seem to be relatively expensive.

Often the deodorizers are contained within a release mechanism package or container which includes a multiplicity of holes that are in some way closed off until the item is put into actual use. When the holes are opened the deodorizers are released by the passage of air through the container thus emitting the activated deodorizer with the naturally circulating air.

Some deodorizer holders have openings that are sealed by plastic packaging materials which are removed when the deodorizer is to be activated. These, cannot, however, be conveniently reclosed. Other deodorizer holders include relatively slidable members for storing and presenting deodorizers for consumer use. These containers are activated by moving inner and outer sections relative to each other, thereby affording alignment of openings in both sections and subsequent release of the contained deodorizer.

Herman F. Guenther, et al, in U.S. Pat. No. 1,074,714 granted on Oct. 7, 1913 for Humidor, shows for example a method for mounting and moistening a pad within a humidor which includes openings. There is, however, no covering means for the openings.

In U.S. Pat. No. 4,279,373 granted to James Montealegre on July 21, 1981 for *Air Freshener Carton,* and U.S. Pat. No. 4,280,649 granted to James Montealegre on July 28, 1981 for *Air Freshener Carton,* there are shown, for example, containers with openings and slidable covers which allow the openings in the containers to be either exposed or covered as desired. However, the body of the slidable cover itself must be grasped to effect a sliding movement thereof to uncover and cover the openings. This limits use of this type of device to situations where the entire device or a significant portion is exposed to permit such movement of the cover.

U.S. Pat. No. 4,523,870 granted to Donald Spector on June 18, 1985 for *Aroma-Dispensing Cartridge and Holder Assembly for Automobiles* shows a cartridge which is attachable to an air vent of an automobile. The cartridge is secured across the force of the automobile air-vent thus significantly obstructing air flow in the cartridge closed condition. In addition, a relatively complex and costly spring type detenting mechanism is required to open and close the cartridge.

SUMMARY OF THE INVENTION

It is therefore an object of this invention to provide a new and improved deodorizer container.

It is another object of this invention to provide a new and improved deodorizer container having relatively slidable members and openings that are exposed and closed thereby;

It is yet another object of this invention to provide a new and improved deodorizer container wherein the relatively slidable members include guide teats and grooves to facilitate operation thereof;

It is still another object of this invention to provide a new and improved deodorizer container wherein the relatively slidable members are detented to each other to control separation thereof.

It is still yet another object of this invention to provide a new and improved deodorizer container wherein a tab extends from the cover member to facilitate movement thereof with respect to the bottom member.

This invention involves a deodorant dispenser having six sides, with holes deployed in two sides and a top surface thereof, containing grooves in the sides with holes for holding a three sided cover thereon and an extending tab for sliding the cover to an open or closed position and of a size to fit within an air duct of an automobile or the like.

Other object, features and advantages of the invention in its details of construction and arrangement of parts will be seen from the above from the following description of the preferred embodiment when considered with the drawing and from the appended claims.

BRIEF DESCRIPTION OF THE DRAWING

In the drawing:

FIG. 1 is a schematic prospective of an automobile dashboard showing a deodorizer container, incorporating the instant invention, in position in an air-flow louvre thereof;

FIG. 2 is an enlarged prospective view of the encircled area 2 of FIG. 1, enlarged to better show details of the deodorizer container;

FIG. 6 is a cross sectional view of the deodorizer container taken at line 6—6 of FIG. 2.

DESCRIPTION OF THE PREFERRED EMBODIMENT

Figure 3:
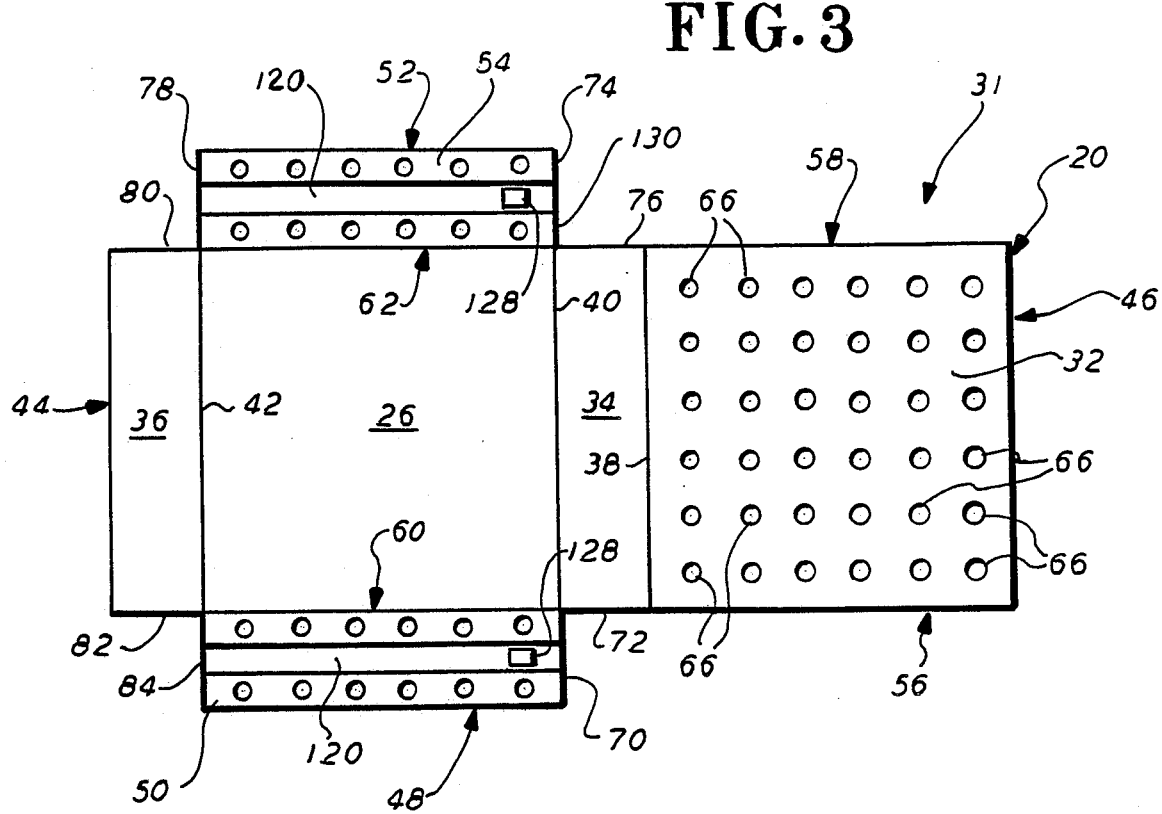
FIG. 3 is a plan view of the blank for forming the bottom for the deodorizer container of FIG. 2.

With reference to FIG. 1, there is shown at 10 a deodorizer container deployed within a set of louvres 12 of a vent 14 mounted within an automobile dashboard 16. While container 10 is shown so disposed it should be understood that it may just as conveniently be disposed in the louvre for any heating or air-conditioning system, unit or the like; in any similar opening, or for that matter in any location where air is moving or to move.

Container 10 (FIGS. 1 and 2) is comprised of a cover 18 slidably attached to a bottom 20; the two being of a predetermined length, height, and width particularly sized, in this instance, to fit within the space 21 between blades 22 of louvre 12. Container 20 is secured to a louvre blade 22 by an attaching device such as, Velcro tape 23, or the like. A first side 24 of Velcro tape 23 is attached to an under-surface, of base 26 of container bottom 20 and a second side 28 of Velcro tape 23 is attached to a top surface 30 of louvre blade 22. Side 24 and side 28 coact to hold container 10 on blade 22.

In FIG. 3 a blank 31, for forming container bottom 20, is shown to include a top 32 of rectangular shape, a side 34 of rectangular shape, base 26 of rectangular shape and a side 36 of rectangular shape and essentially the same size and configuration as side 34. Side 34 and top 32 join at an edge 38 which is common to both. An edge 40 is common to side 34 and base 26. Base 26 is essentially the same size and geometric configuration as top 32. An edge 42 is common to base 26 and side 36. An end edge 44 and an bottom edge 46 are co-linear when blank 31 is formed to become container 20. Similarly a side edge 48 of a side 50 carried by base 26 and a side edge 52 of a side 54 respectively are co-linear with a side edge 56 and a side edge 58 also of top 32.

Sides 50 and 52 are of essentially the same size and configuration having a predetermined length and width corresponding respectively to bottom 26, top 32, side 34 and side 36. An edge 60 is formed common to base 26 and side 50. An edge 62 is formed common to base 26 and side 54. Edges 38, 40, 42, 60 and 62 may be perforated, creased or otherwise similarly prepared for bending during manufacture. Blank 31 may be fabricated, from hardboard, plastic, cardboard or the like using steel rule die cutting, rotary die cutting, or similar applicable manufacturing methods. A multiplicity of holes 66 of predetermined size and arrangement to facilitate the proper release of deodorant are deployed through top 32, side 50 and side 54, by die cutting, drilling, punching or the like.

To form bottom 20 sides 34 and 36 are bent up from base 26 along edges 40, 42 respectively; and sides 50 and 52 are bent up from base 26 along edges 60, 62 respectively. Top 32 is bent over along edge 38 to form container bottom 20 into a six-sided container. When so formed common edges 44 and 46, 48 and 56, and 52 and 58 will be disposed proximate each other and may be attached or closed by glueing, bonding or the like. In addition, common intermediate edges 70 and 72, 74 and 76, 78 and 80 and 82 and 84 will also be disposed proximate each other and may be similarly closed together or attached. Prior to so forming bottom 20 of deodorizer container 10 a deodorant or deodorizer 68 in the form of a solid, saturated pad or the like should be placed in a position to be enclosed within the finally formed container bottom 20.

Figure 4:
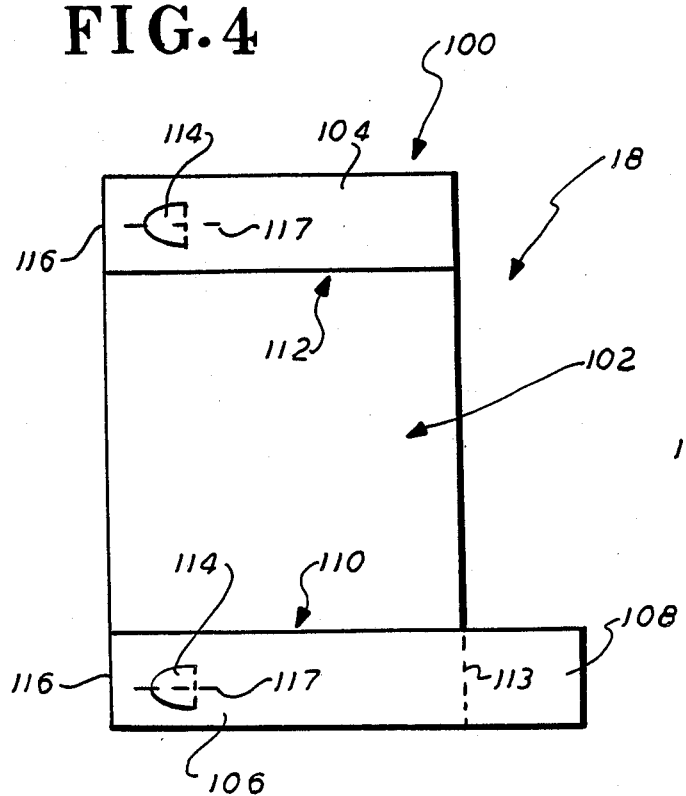
FIG. 4 is a plan view of the blank for forming a cover for the deodorizer container of FIGS. 2 and 3.

A blank 100, for forming container cover 18, is shown in FIG. 4 as comprised of a top 102, a side 104, a side 106 and a tab 108. Top 102 is essentially the same size as top 32 of container bottom 20, plus a small increment, to facilitate disposition of sides 104 and 106 so that they are parallel to each other and to sides 50 and 54 of container bottom 20 (when formed perpendicular to top 102 along a pair of edges 110 and 112) and so that sides 104, 106 envelop sides 50 and 54 respectively when cover 18 is disposed on container bottom 20. To form cover 18 sides 102, 104 are bent along edges 110, 112 respectively and tab 108 is bent outwardly along edge 113 to form the configuration shown in FIG. 5.

Figure 5:
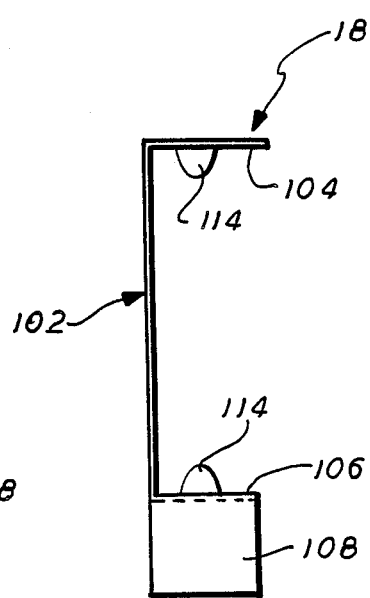
FIG. 5 is a side view of the deodorizer container cover after being formed.

A set of teats 114 are formed proximate a first end 116 of sides 104 and 106 and so as to extend therefrom (FIG. 5). Tests 114 are formed to extend inwardly towards each other in the final formed configuration of cover 18 (FIG. 5). They are furthermore formed to a size and configuration to be disposed in and to move along a pair of grooves, formed in sides 50, 54 of container bottom 20, and to each coact with a detent 128 each disposed proximate an end 130 of sides 50, 54 respectively. Tests 114 are furthermore formed along a set of creased lines 117 and deployed within grooves 120 when to cover 18 is assembled to container bottom 20.

Grooves 120 (FIG. 3 and FIG. 6) are each substantially in the shape of a "U" when formed and are essentially central to the height of sides 50 and 54 and traverse to the length of sides 50 and 54. Detents 128 are each disposed central to the width of grooves 120.

Cover 18 and container bottom 29 are assembled to each other with end 116 of cover 18 and end 130 of container bottom 20 opposite each other. Cover 18 is restrained from separating from container bottom 20 by the coaction of teats 114 and detents 128.

In use deodorizer container 10 is disposed within the space between a pair of louvre blades 23, such as blades 22 of an automobile, by attaching the first side 24 of Velcro 23 that is carried by container base 26 to the second side 28 of Velcro 23 that is attached to louvre blade 22. Tab 108 is disposed to be accessable when container 10 is so disposed and so that by grasping tab 108 container cover 18 can be slid with respect to container bottom 20 to expose holes 66 and permit the air flowing from louvre 22 to draw the deodorant from container 10. If desired tab 108 can be used to slide cover 18 in the opposite direction to close container 10.

It should be understood that although container 10 is preferably shown as disposed between the louvres of an automobile air system that container 10 may just as easily be disposed between louvres in any air-conditioning circulating or heating system or for that matter individual units for doing so. It should further be understood that container 10 may just as easily be attached to a wall, table, cabinet or other surface which places same in an air flow.

While container 10 has been shown and described as being formed from blanks that are formed into a container cover 18 and a container bottom 20 it should be realized that said container cover and bottom may each be formed of plastic or similar material molded into the respective final configurations.

From the above, it will thus be seen that there has been provided a novel and improved deodorizer container which is relatively simple in construction and is of a size which can be deployed within an air vent louvre of an automobile or the like or otherwise as desired.

It is understood that although I have shown the preferred form of my invention that various modifications may be made in the details thereof without departing from the spirit as comprehended by the following claims.

I claim:

1. A deodorizer container; comprising:
   (a) container bottom means of a predetermined size and a predetermined configuration so as to form an enclosure for containing a deodorant and having one or more openings formed herethrough.
   (b) container cover means of a predetermined size and a predetermined configuration whereby said container cover means encapsulates at least a portion of said container bottom means and is carried thereby for selected movement between a first position wherein said one or more openings are covered and a second position wherein said one or more openings are exposed; and
   (c) tab means laterally extending from said container cover means to push or pull said container cover means between said first position and said second position.

2. The deodorizer container of claim 1, wherein said predetermined configuration of said container bottom means is that of a substantially right parallelapiped.

3. The deodorizer container of claim 2, wherein said predetermined configuration of said container cover means is one of substantially "U" shape.

4. The deodorizer container of claim 3, guide means are carried by said container bottom means and said container cover means to facilitate said selected movement of said container cover means.

5. The deodorizer container of claim 4, wherein said guide means includes groove means carried by said container bottom means and cooperating teats carried by said container cover means.

6. The deodorizer container of claim 5, including detent means formed in said groove means for cooperation with said cooperating teats to limit said selected movement of said container cover means so that it does not readily separate from said container bottom means.

7. The deodorizer container of claim 1, wherein said predetermined size and said predetermined configuration of said container bottom means is such as to facilitate disposition thereof between spaced louvres of an air moving device.

8. The deodorizes container of claim 7 wherein the air moving device is the air conditioning system of an automobile.

9. The deodorizer container of claim 8 wherein attaching means are provided for securing the deodorizer container to a surface of at least one louvre of the air moving device.

10. The deodorizer container of claim 9 wherein said container bottom means and said container cover means extend into the space between the spaced louvres but so that said tab means remains accessable to facilitate moving said cover means.

11. The deodorizer container of claim 10 wherein said attaching means secures said container bottom means to the louvre.

12. The deodorizer container of claim 11 wherein said attaching means includes cooperating Velcro-type attaching elements one of which is carried by said container bottom means and the other of which is carried by the louvre.

13. The deodorizer container of claim 1 wherein said tab means extends at a right angle from said container cover means.

14. The deodorizer container of claim 1 wherein said container bottom means is in the configuration of a substantially right parallelapiped including at least a top and a pair of opposed sides and said openings extend through said top and said opposed sides.

15. The deodorizer container of claim 13 wherein there are a plurality of said openings extending through said top and said opposed sides.

* * * * *